United States Patent
Biber et al.

(10) Patent No.: US 11,333,724 B2
(45) Date of Patent: May 17, 2022

(54) APPARATUS AND METHOD FOR REAL-TIME MONITORING AND CONTROL OF LOCAL COILS

(71) Applicant: Siemens Healthcare GmbH, Erlangen (DE)

(72) Inventors: Stephan Biber, Erlangen (DE); Nikolaus Demharter, Dormitz (DE); Franz Eiermann, Rattelsdorf (DE); Klaus Porzelt, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/109,383

(22) Filed: Dec. 2, 2020

(65) Prior Publication Data

US 2021/0190890 A1 Jun. 24, 2021

(30) Foreign Application Priority Data

Dec. 18, 2019 (DE) .......................... 102019220054.0

(51) Int. Cl.
| | | |
|---|---|---|
| G01R 33/36 | (2006.01) | |
| G01R 33/54 | (2006.01) | |
| G01R 33/48 | (2006.01) | |
| A61B 5/055 | (2006.01) | |

(52) U.S. Cl.
CPC ..... *G01R 33/3628* (2013.01); *G01R 33/4812* (2013.01); *G01R 33/543* (2013.01); *A61B 5/055* (2013.01)

(58) Field of Classification Search
USPC ........................................................ 324/313
See application file for complete search history.

(56) References Cited

U.S. PATENT DOCUMENTS

| | | |
|---|---|---|
| 2002/0080911 A1 | 6/2002 | Friedrich |
| 2009/0302845 A1 | 12/2009 | Biber |
| 2014/0210475 A1* | 7/2014 | Li ...................... G01R 33/3628 324/322 |
| 2017/0074953 A1 | 3/2017 | Demharter |
| 2018/0329003 A1 | 11/2018 | Nistler |
| 2021/0088608 A1 | 3/2021 | Biber |

FOREIGN PATENT DOCUMENTS

| | | |
|---|---|---|
| DE | 10051155 A1 | 5/2002 |
| DE | 102008026849 A1 | 12/2009 |
| DE | 102015217723 A1 | 3/2017 |

OTHER PUBLICATIONS

German Office Action for German Application No. 10 2019 220 054.0 dated Oct. 26, 2020.

* cited by examiner

*Primary Examiner* — Rodney E Fuller
(74) *Attorney, Agent, or Firm* — Lempia Summerfield Katz LLC

(57) ABSTRACT

A local coil, a magnetic resonance tomography scanner, a system including local coil and magnetic resonance tomography scanner, and a method for operating the system are provided. The local coil has an active detuning facility and a passive detuning facility with substantially separate circuits. The magnetic resonance tomography scanner includes a local coil actuation for actuating the active detuning facility and a local coil monitoring for the detuning facilities, which likewise have substantially separate circuits.

13 Claims, 5 Drawing Sheets

1 Magnetic resonance tomography scanner
2 Longitudinal direction
10 Magnet unit
11 Field magnet
12 Gradient coils
14 Body coil
16 Patient tunnel
20 Control unit
21 Gradient controller
22 Radio frequency unit
23 Controller
24 Magnet controller
25 Signal bus
30 Patient couch
33 Connecting line
36 Displacement unit
50 Local coil
61 Local coil actuation
62 Local coil monitoring
100 Patient 1   Magnetic resonance tomography scanner
2   Longitudinal direction
10  Magnet unit
11  Field magnet
12  Gradient coils
14  Body coil
16  Patient tunnel
20  Control unit
21  Gradient controller
22  Radio frequency unit
23  Controller
24  Magnet controller
25  Signal bus 30  Patient couch
33  Connecting line
36  Displacement unit
50  Local coil
61  Local coil actuation
62  Local coil monitoring
100 Patient 14 Body coil
22 Radio frequency unit
26 Transmitter
50 Local coil
51 Active detuning facility
61 Local coil actuation
62 Local coil monitoring

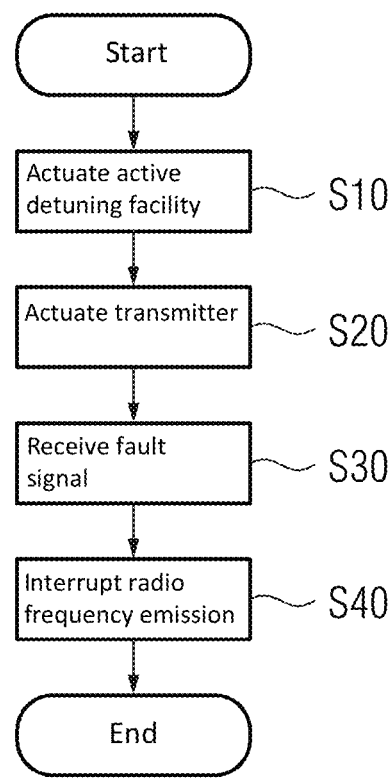

ably, the safety of the local coil is not affected by an individual defect, because in the case of a failure of one of the two detuning facilities, the other detuning facility respectively continues to prevent a risk.
APPARATUS AND METHOD FOR REAL-TIME MONITORING AND CONTROL OF LOCAL COILS The present patent document claims the benefit of German Patent Application No. 10 2019 220 054.0, filed Dec. 18, 2019, which is hereby incorporated by reference.

TECHNICAL FIELD

The disclosure relates to a local coil, a magnetic resonance tomography scanner, and a method for safe operation of the magnetic resonance tomography scanner with the local coil. The local coil has active and/or passive detuning facilities.

BACKGROUND

Magnetic resonance tomography scanners are imaging apparatuses, which for imaging an examination object orient nuclear spins of the examination object with a strong external magnetic field and by way of a magnetic alternating field excite them to precession about this orientation. The precession or return of the spins from this excited state into a state with lower energy in turn generates a magnetic alternating field in response, which is received via antennas.

With the aid of magnetic gradient fields, a spatial encoding is impressed on the signals, and this subsequently makes it possible to allocate the received signal to a volume element. The received signal is then evaluated and a three-dimensional image-based representation of the examination object is provided.

To achieve sufficient excitation, the magnetic alternating field may reach powers of several hundred watts up to kilowatts for excitation of the nuclear spins. The field strengths that occur in the process may endanger the patient due to thermal effects. Even more direct electrical effects and disruptions, (e.g., in the case of implants such as electronic pacemakers), are particularly critical owing to the rapid onset. Damage may occur during a single excitation pulse already here.

SUMMARY AND DESCRIPTION

It is an object of the present disclosure to make an examination with a magnetic resonance tomography scanner safer, therefore.

The object is achieved by local coil, a magnetic resonance tomography scanner, a system, a method for operation, and a magnetic resonance tomography scanner. The scope of the present disclosure is defined solely by the appended claims and is not affected to any degree by the statements within this summary. The present embodiments may obviate one or more of the drawbacks or limitations in the related art.

The local coil has an active detuning facility and a passive detuning facility. A circuit in the local coil is referred to as an active detuning facility in this connection, which varies a resonance frequency of the local coil in response to an actuation signal, so it is no longer resonant at a Larmor frequency of the magnetic resonance tomography scanner. The resonance frequency of the local coil is varied by the activated active detuning facility to the extent that an amplitude of an induced signal with Larmor frequency of the magnetic resonance tomography scanner is damped by more than 20 dB, 40 dB, 60 dB, or 80 dB with respect to the amplitude without active or passive detuning. For detuning or damping, the passive detuning facility uses the induced voltage and limits it to a safe value, (e.g., less than 2V, 5V, 10V, or 20V). The passive detuning facility and the active detuning facility have substantially separate circuits. Within the meaning of the disclosure, "substantially separate circuits" should be taken to mean that there is no individual defect in the local coil, which simultaneously prevents the proper functioning of the active detuning facility and the passive detuning facility and nevertheless still allows a resonance of the local coil at the Larmor frequency. An interruption of the antenna circuit of the local coil may prevent proper functioning of the detuning facilities, but simultaneously not constitute a risk because even without detuning no resonances would occur. An individual defect may also be referred to as a "single point of failure."

Advantageously, the safety of the local coil is not affected by an individual defect, because in the case of a failure of one of the two detuning facilities, the other detuning facility respectively continues to prevent a risk.

The magnetic resonance tomography scanner has a local coil actuation and a local coil monitoring. In particular, a circuit, which actuates an active detuning facility of a local coil and thus, controlled by a controller of the magnetic resonance tomography scanner, may purposefully detune the local coil or may also restore it to the resonance frequency, is regarded as a local coil actuation here. This may be achieved in that in the local coil, a PIN diode is provided in the antenna circuit. This reduces the capacitance by way of a voltage applied by the local coil actuation and thus detunes the antenna circuit. An applied, forward current is also conceivable, by which the PIN diode becomes conductive and thus switches or directly short-circuits, for example, an additional capacitor in the antenna circuit.

A circuit, logic, or program on a processor or a combination thereof is regarded as a local coil monitoring, which is configured to establish proper functioning of the local coil actuation and the passive and/or active detuning facility in real time. This may take place by monitoring a voltage at the PIN diode and/or a current through the PIN diode, so an interruption of the connection or malfunctioning of the PIN diode may be established. It would also be conceivable to detect an amplitude of a voltage in the resonance circuit.

The local coil actuation and the local coil monitoring have substantially separate circuits. As already explained in relation to the local coil, this should be taken to mean that there is no "single point of failure" in circuit or components of local coil actuations and local coil monitoring, which prevents correct actuation of the detuning facility, simultaneously prevents recognition of this fault in the local coil monitoring and due to resonance in the antenna circuit of the local coil may put the patient at risk, moreover.

In one embodiment, the magnetic resonance system has a body coil control and a body coil monitoring system. In particular, a circuit, which actuates an active detuning facility of a body coil and thus, controlled by a controller of the magnetic resonance tomography scanner, may purposefully detune the body coil or also restore it to the resonance frequency, is regarded as a body coil control here. This may be achieved in that, on the body coil, a PIN diode is provided in the antenna circuit and this reduces the capacitance by way of a voltage applied by the body coil control and thus detunes the antenna circuit. An applied, forward current is also conceivable, by which the PIN diode becomes conductive and thus switches or directly short-circuits, for example, an additional capacitor in the antenna circuit.

Advantageously, the magnetic resonance tomography scanner provides by way of independent local coil actuation and local coil monitoring or body coil control and body coil monitoring that the patient is not exposed to danger due to a single failure of one component.

The method is provided for operating a system including a magnetic resonance tomography scanner and a local coil. In one act, the local coil monitoring receives a fault signal at the detuning monitoring input of the local coil monitoring. The fault signal signals malfunctioning of the active detuning facility and/or passive detuning facility of the local coil. This also incorporates malfunctioning of the feedback from the active detuning facility and/or passive detuning facility, for example, if a signal link from the local coil back to the local coil monitoring is interrupted.

The fault signal may be a voltage or a current or the absence thereof. For example, an excessively high voltage may indicate that a PIN diode is defective, or the feed line is interrupted. If no voltage is applied, then this may also indicate an interruption of the return connection. A monitoring circuit in the local coil, which encodes a status of the active detuning facility and/or passive detuning facility into an analog or digital signal would also be conceivable, however.

In a further act of the method, the local coil monitoring interrupts a radio frequency emission. This may take place indirectly, but with priority, via the controller of the magnetic resonance tomography scanner and a radio frequency controller. Direct connections or circuit breakers, which directly prevent emission, are also conceivable. If, at the instant of the interruption itself, there is no radio frequency emission, but a subsequent radio frequency emission is also prevented, then this is also regarded as an interruption.

Advantageously, the method provides that in event of a malfunction in the detuning of the local coil or its monitoring system, there is no further radio frequency emission.

Similarly, in one embodiment of the method, a fault signal of the body coil monitoring system may interrupt or prevent a radio frequency emission as a reaction to malfunctioning of the body coil.

In one possible embodiment of the local coil, a component necessary for detuning is designed redundantly in the active detuning facility and/or passive detuning facility. Any components whose failure prevent detuning of the local coil in a framework necessary for the safety of the patient are regarded as components essential to detuning. In each case, the component is regarded as if it were part of the, in each case, only detuning facility, in other words, without considering a different detuning facility as redundancy. Thus, for example, the active detuning facility, the passive detuning facility, and also a possible fuse are separately considered. In one embodiment, a plurality of components or all components necessary for detuning in one, a plurality of or all detuning facilities is designed redundantly.

The components may be capacitors, which vary the resonance frequency or short-circuit a radio frequency signal. Possible components are also diodes or PIN diodes, which controllably vary the capacitor or switch a radio frequency signal. Inductances may also be designed redundantly. Components with a high probability of failure may be configured redundantly, such as diodes, which may fail in the case of an excessively high current or an excessively high voltage and degrade over time. Capacitors may also have a tendency to short-circuit and fail as a result of ageing or overvoltage.

Depending on the type of the most probable failure of a component or its required function, a redundancy may be achieved by serial and/or parallel arrangement of two similar components.

In a comparable manner, a detuning facility of the body coil may be configured redundantly.

Advantageously, the redundant design of critical components fundamentally improves the functional safety of the detuning facility.

In one conceivable embodiment of the local coil, the local coil has at least one monitoring signal output for a monitoring signal. The local coil is configured to signal a functional status of the passive detuning facility and/or active detuning facility with the monitoring signal. The monitoring signal may be derived from a voltage or a current, which is applied at a PIN diode or flows through it. It would also be conceivable to make the monitoring signal dependent on an effect of the detuning facility, for example, in that the monitoring signal is dependent on a voltage induced in the antenna coil. The signal may also be prepared by logic circuit or algorithms and encode information about the status of the detuning facility, for example, digitally. An optical signal would also be conceivable to circumvent problems with sheath waves using an optical fiber or wireless transmission, e.g., at frequencies above the Larmor frequency of the magnetic resonance tomography scanner, such as in an ISM band. For example, Bluetooth or WLAN are conceivable. With a radio transmission, the absence of the signal from the local coil monitoring may be interpreted as a fault state of the detuning facility in order to not endanger the patient in the event of simultaneous failure of the detuning facility.

Advantageously, the local coil, with the monitoring signal output, provides a way, which is independent of the actuation, of reliably recognizing a malfunction in the event of a fault.

Similarly, a monitoring signal output of the body coil monitoring system may also monitor tuning or detuning of the body coil and display malfunctioning of the body coil control.

In one possible embodiment of the magnetic resonance tomography scanner, the magnetic resonance tomography scanner has a controller. The local coil monitoring also has a first direct signal link to the controller. A direct signal link is in this case taken to mean a signal link, which cannot be temporarily blocked or, in the event of a fault, even completely blocked by other sub-units of the magnetic resonance tomography scanner. This may be a direct electrical signal line in a point-to-point or star configuration, but may also be a bus system, which is secured by protocol and logic against blockages and failures of this kind.

The controller is configured to interrupt a radio frequency emission in response to a warning signal from the local coil monitoring via the first direct signal link. A warning signal is regarded as any signal with which the local coil monitoring signals a fault in the active and/or passive detuning facility or a fault in the monitoring system. As already explained in a different connection, the warning signal may be transmitted or encoded in an analog or a digital manner.

The controller can, however, also be configured to interrupt a radio frequency emission in response to a warning signal from the body coil monitoring system via the first direct signal link. A warning signal is regarded as any signal with which the body coil monitoring system signals a fault in the active and/or passive detuning facility or a fault in the monitoring system. As already explained in a different connection, the warning signal may be transmitted or encoded in an analog or a digital manner.

Advantageously, the direct signal link provides that the interruption of the radio frequency emission takes place with priority and also reliably and quickly in the case of individual faults in the monitoring system.

In one conceivable embodiment of the magnetic resonance tomography scanner, the controller has a second direct signal link to a radio frequency controller. That which was stated in relation to the first direct signal link applies in respect of the term "directly". The radio frequency controller is configured to directly interrupt a radio frequency emission in response to an interrupt signal of the controller via the second direct signal link. In this case, directly is taken to mean that the radio frequency controller does not wait for an excitation pulse to playout first. Instead, in particular with an instantaneously active emission, interrupts this in an optimally short time. It would be conceivable, for example, for an actuation signal for a power output stage, or even an energy supply for the power output stage, to be interrupted.

Advantageously, the direct signal link between controller and radio frequency controller provides fast and reliable interruption of the radio frequency emission.

In one possible embodiment of the system, the local coil monitoring is configured to receive a fault signal at the detuning monitoring input from the local coil. The fault signal in this case signals malfunctioning of the active detuning facility and/or the passive detuning facility to the local coil. The local coil monitoring is also configured to send a warning signal for interruption of the radio frequency emission to the controller via the first direct signal link.

Advantageously, the system including local coil and magnetic resonance tomography scanner is capable of exchanging fault signals via a signal link between monitoring signal output and detuning monitoring input. Further, in the event of a fault, the system is capable of interrupting an interruption of the radio frequency emission for the safety of the patient.

In one conceivable embodiment of the method, the magnetic resonance tomography scanner firstly begins a radio frequency emission in a preceding act.

In other words, it also is possible to monitor the active and/or passive detuning facility during emission of a radio frequency signal or excitation pulse because separate test pulses are not used here to recognize faults. Advantageously, permanent monitoring and rapid response in the event of faults in the detuning facility is thus possible.

In an embodiment, the magnetic resonance tomography scanner firstly actuates the active detuning facility in the local coil in a preceding act.

Advantageously, active detuning of the local coil during the radio frequency emission minimizes adverse effects of the local coil on imaging due to spatial variation of the field strengths, and therewith of the excitation of nuclear spins.

BRIEF DESCRIPTION OF THE DRAWINGS

The above-described properties, features, and advantages of this disclosure and the manner in which they are achieved will become clearer and more comprehensible in conjunction with the following description of the exemplary embodiments, which will be explained in more detail in connection with the drawings, in which:

FIG. 5 depicts a schematic flowchart of an embodiment of the method.

DETAILED DESCRIPTION

Figure 1:
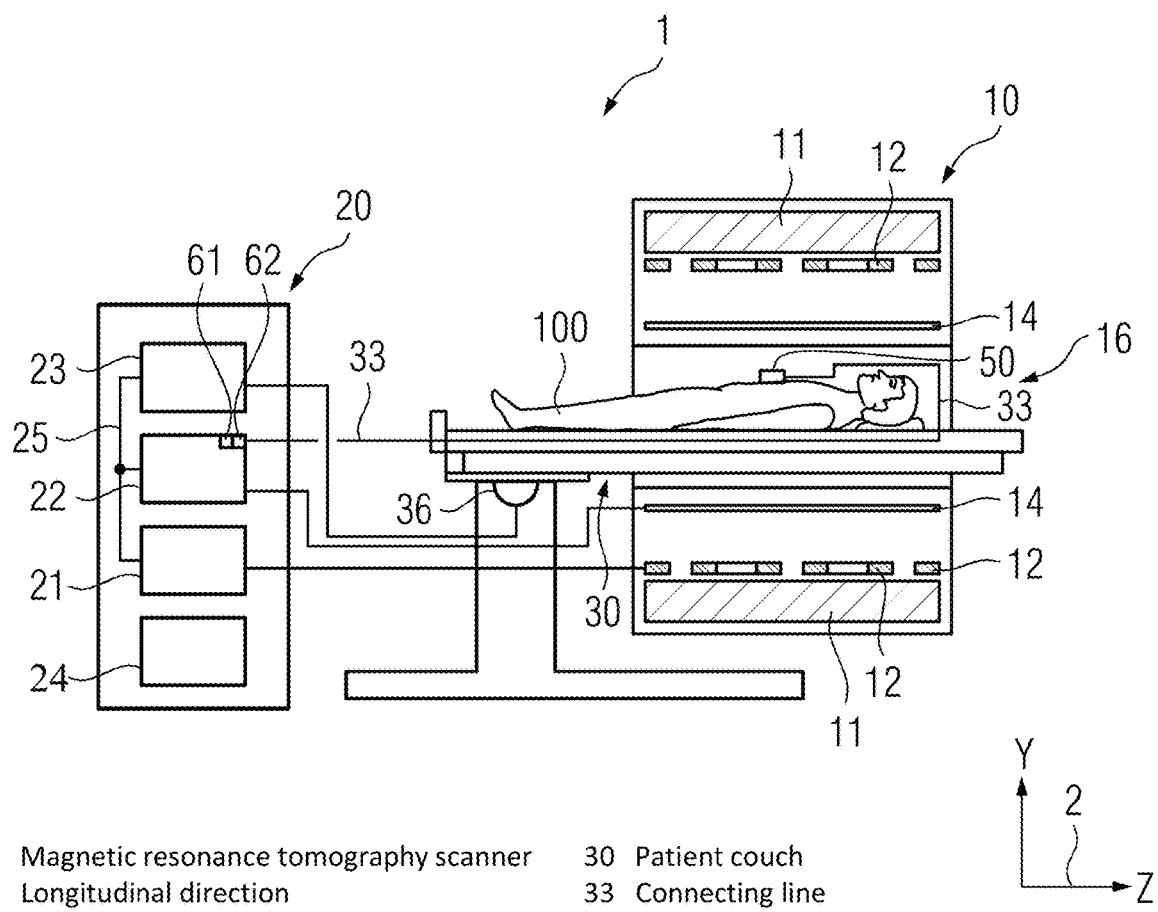
FIG. 1 depicts a schematic diagram of an embodiment of a magnetic resonance tomography scanner.

FIG. 1 depicts a schematic diagram of an embodiment of a magnetic resonance tomography scanner 1.

The magnet unit 10 has a field magnet 11, which generates a static magnetic field B0 for the orientation of nuclear spins of samples or of the patient 100 in a recording region. The recording region is characterized by an extremely homogeneous static magnetic field B0, with the homogeneity relating, in particular, to the magnetic field strength or value. The recording region is almost spherical and arranged in a patient tunnel 16, which extends in a longitudinal direction 2 through the magnet unit 10. A patient couch 30 may be moved in the patient tunnel 16 by the displacement unit 36. The field magnet 11 is conventionally a super-conducting magnet, which may provide magnetic fields with a magnetic flux density of up to 3T, and even above this in the newest devices. Permanent magnets or electromagnets with normal-conductive coils may also be used for lower field strengths, however.

The magnet unit 10 also has gradient coils 12, which are configured to overlay the magnetic field B0 with variable magnetic fields in three spatial directions in order to spatially differentiate the captured imaging regions in the examination volume. The gradient coils 12 are conventionally coils including normal conducting wires, which may generate fields in the examination volume which are orthogonal to each other.

The magnet unit 10 likewise has a body coil 14, which is configured to irradiate a radio frequency signal fed via a signal line into the examination volume and to receive resonance signals emitted by the patient 100 and deliver them via a signal line.

A control unit 20 supplies the magnet unit 10 with the various signals for the gradient coils 12 and the body coil 14 and evaluates the received signals.

The control unit 20 has a gradient controller 21, therefore, which is configured to supply the gradient coils 12 via feed lines with variable currents, which provide the desired gradient fields in the examination volume so as to be coordinated time-wise.

The control unit 20 also has a radio frequency unit 22, which is configured to generate a radio frequency pulse with a specified course over time, amplitude, and spectral power distribution for exciting a magnetic resonance of the nuclear spins in the patient 100. Pulse powers in the region of kilowatts may be achieved in the process. The excitation pulses may be irradiated via the body coil 14 or also via a local transmit antenna into the patient 100.

A local coil 50 is arranged on the patient 100 and is connected by a connecting line 33 to the radio frequency unit 22.

A magnet controller 24 monitors the field magnet 11. In an embodiment, the magnet controller 24 is also configured to move, the field B0 of the superconducting magnet up and down in a controlled manner.

A controller 23 communicates via a signal bus 25 with the gradient controller 21, the radio frequency unit 22, and the magnet controller 24 and coordinates their activities in particular during image recording.

The radio frequency unit 22 also controls the local coil 50. In particular, the radio frequency unit 22 has a local coil actuation 61, which activates and deactivates an active detuning facility via a signal link by way of a signal. The radio frequency unit 22 also has a local coil monitoring 62, which monitors the functioning of the active detuning facility 51 and/or a passive detuning facility 52 of the local coil 50 via a signal link. Details on the signal link and the local coil 50 are explained in relation to the Figures below.

The radio frequency unit 22 also has one or more receiver(s) to prepare magnetic resonance signals received from the local coil 50 or the body coil 14 for image recording and forward them to the controller 23 or a separate arithmetic unit for image reconstruction.

Figure 2:
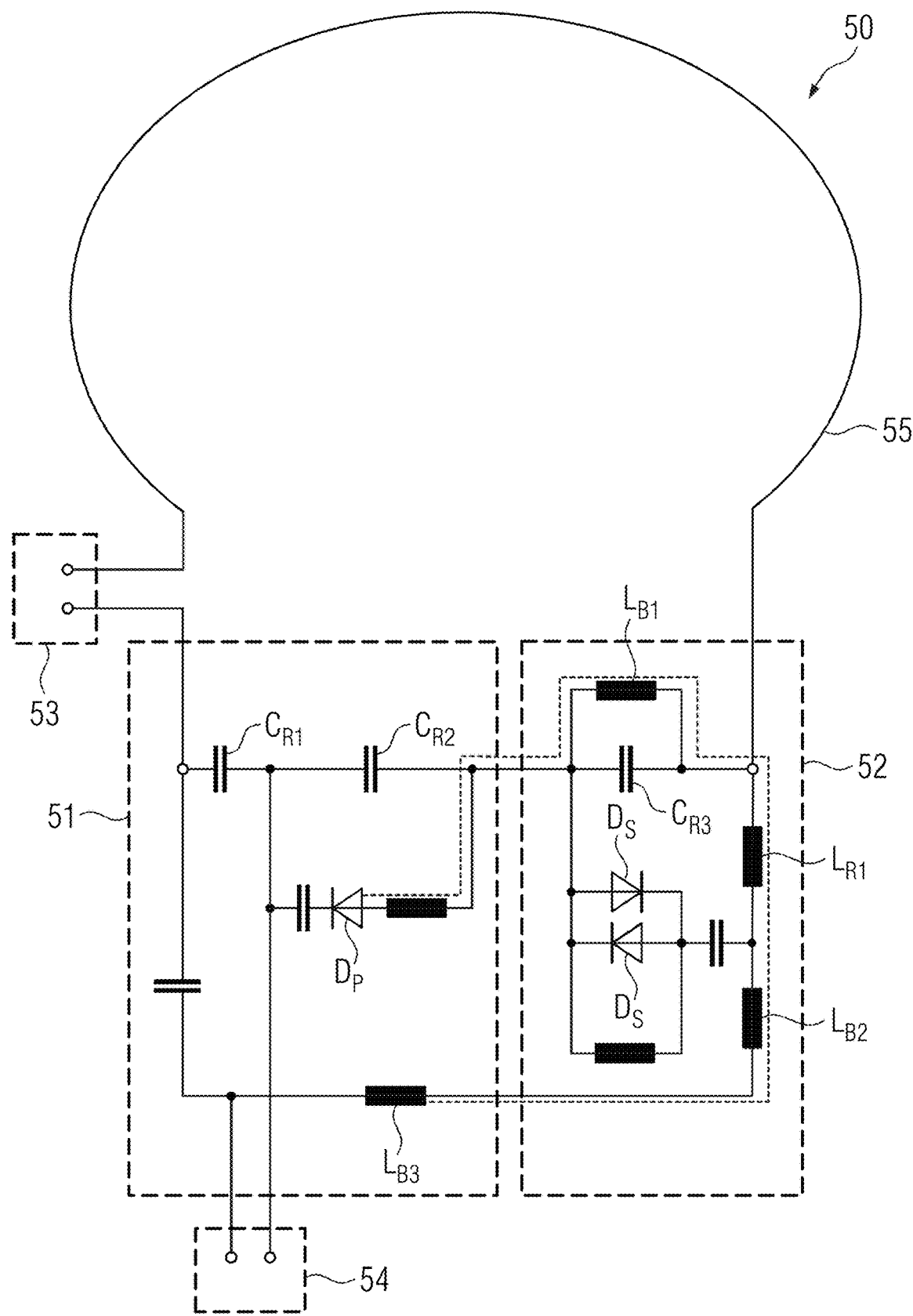
FIG. 2 depicts a schematic diagram of one possible embodiment of an active detuning facility and a passive detuning facility of a local coil.

FIG. 2 schematically illustrates one possible embodiment of an active detuning facility 51 and a passive detuning facility 52 of a local coil 50. In FIG. 2, the components and electrical connections of the active detuning facility 51 are largely separate.

For receiving magnetic resonance signals, an inductive antenna coil 55 is provided, which may also have a plurality of windings. A received radio frequency signal may be tapped via the RF signal connection 53. Conventionally, an impedance adjustment, pre-amplification by a low-noise pre-amplifier (LNA), and optionally frequency conversion and/or digitization of the received magnetic resonance signal still take place downstream of the RF signal connection 53. These signal processing acts are not shown for the sake of clarity.

The active detuning facility 51 and the passive detuning facility 52 are connected in series with the antenna coil 55. The resonance capacitors denoted by $C_R$, together with the inductance of the antenna coil thus form a series resonance circuit.

A direct current or a direct voltage may be fed via a detuning connection 54 in order to vary the resonance frequency of the antenna circuit including the antenna coil 55 and the resonance capacitors $C_R$ by the active detuning facility 51. As a varying element, a PIN diode $D_P$ with voltage-dependent capacitor and an inductor may be connected parallel to a resonance capacitor $C_{R3}$. A direct voltage or a direct current may be applied to the PIN diode $D_P$ via the path marked with points next to the line link via the detuning connection 54. The inductors identified by $L_B$ are used solely for the purpose of blocking a radio frequency signal and let only the control voltage or the control current through. A reverse voltage reduces the capacitance of the PIN diode $D_P$, while a forward current allows this to act through the PIN diode $D_P$ as a short-circuit or conductor. In both cases, the resonance frequency of the local coil 50 changes.

The passive detuning facility 52 has a parallel loop including a capacitor, two diodes $D_S$, and two inductors to the capacitor $C_{R3}$. The two diodes $D_S$ are connected in antiparallel, so an applied alternating voltage above a diode-specific threshold voltage is passed on while, for low alternating voltages, such as the received MR-signals, the diodes act like a constant capacitor. The parallel loop acts as a series resonance circuit connected in parallel to the capacitor $C_{R3}$ with resonance frequency dependent on the amplitude or, with a constant frequency, as an amplitude-dependent impedance, which detunes the antenna coil between two limit frequencies, therefore. In this way, a voltage, induced in the local coil 50 by an excitation pulse, or current may also be limited without an active control signal by way of the passive detuning facility.

The active detuning facility 51 and the passive detuning facility 52 share the radio frequency signal path along the capacitors $C_{R1}$, $C_{R2}$, and $C_{R3}$ in the resonance circuit formed with the antenna coil 55. If a capacitor or a connector fails here, the resonance circuit is also simultaneously interrupted thereby, and it is not possible for dangerous voltages to build up.

The inductor $L_{R1}$ in the direct current path of the active detuning facility 51 is still also part of the radio frequency path of the passive detuning facility 52. If an interruption occurs here, the impedance of the loop lying parallel to $C_{R3}$ also changes, however, and thus leads to detuning of the resonance circuit of the antenna coil 55. The probability of failure for an inductor, which is composed substantially of just one wound wire, is very low, moreover.

Advantageously, the local coil 50 in FIG. 2 thus has no "single point of failure" for the detuning facilities, which may put the patient 100 at risk.

Figure 3:
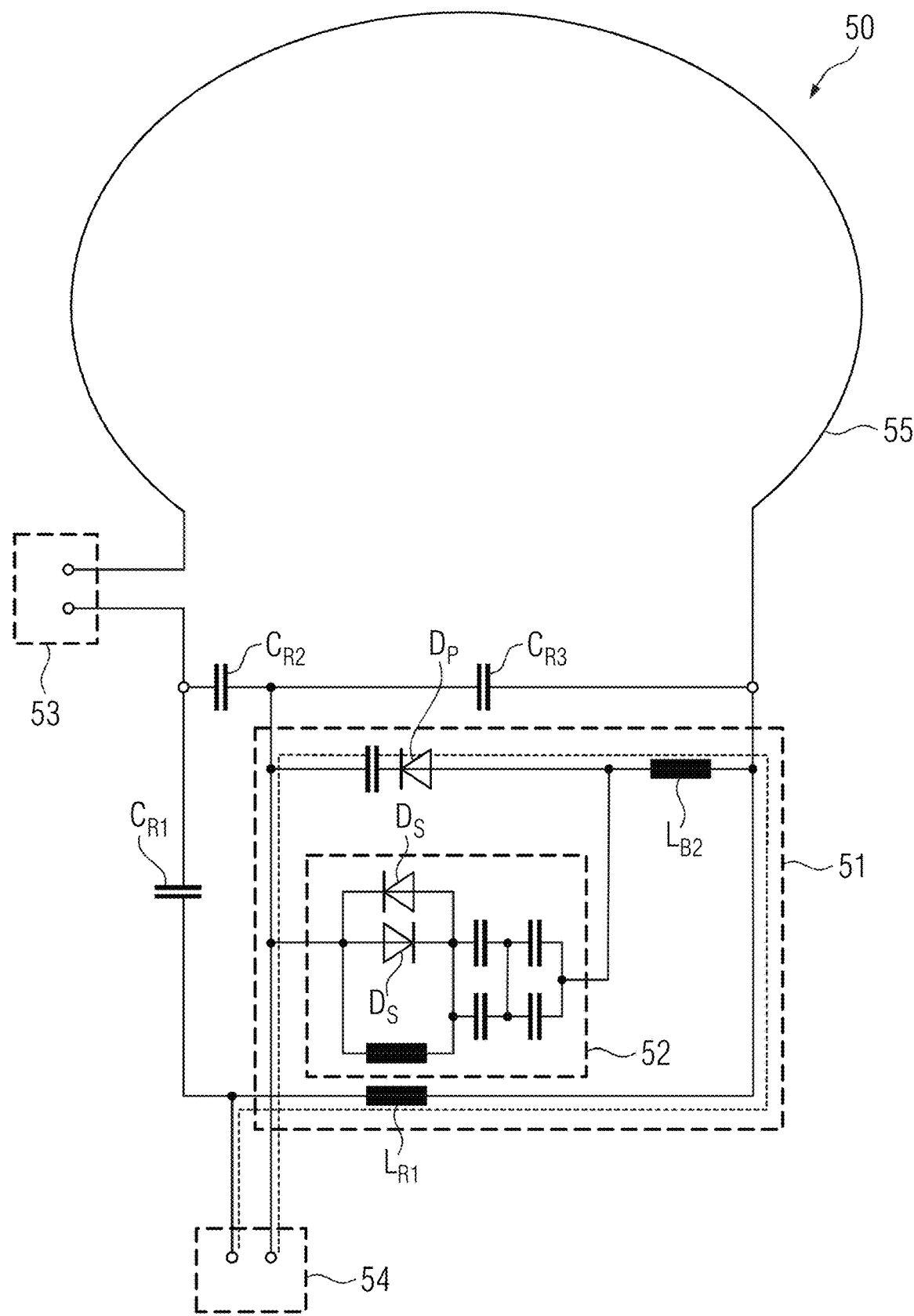
FIG. 3 depicts a schematic diagram of one possible embodiment of an active detuning facility and a passive detuning facility of a local coil.

FIG. 3 schematically illustrates one possible embodiment of an active detuning facility 51 and a passive detuning facility 52 of a local coil 50 in which the active detuning facility 51 and the passive detuning facility 52 are even more strongly interlocked with each other and thus save on components, but nevertheless do not have a "single point of failure". Functionally comparable components are again designated by the same reference characters even if their dimensions may differ between FIG. 2 and FIG. 3.

It is not possible to illustrate a separation as easily here. In FIG. 3, the passive detuning facility 52 is thus inside the active detuning facility 51. While the components of the passive detuning facility 52 may be allocated to it and are not necessary for the functionality of the active detuning facility 51, due to the parallel connection to the PIN diode $D_P$ of the active detuning facility 51, the impedance of the passive detuning facility 52 still affects the impact of the active tuning facility on the resonance frequency of the resonance circuit of the antenna coil 55 with the series capacitors $C_{R1}$, $C_{R2}$, and $C_{R3}$. As the values of these capacitors, the impedances of the active detuning facility 51 in the non-actuated state and the passive detuning facility 52 with low-level signals below the forward voltage of the diodes DS are selected such that the resonance circuit of the antenna coil 55 with these elements lies at the Larmor frequency of the magnetic resonance tomography scanner 1, even in the event of an interruption of a shared connection of the active detuning facility 51 and the passive detuning facility 52 to the antenna coil due the missing impedance, connected in parallel, of the detuning facilities, the resonance circuit is detuned such that no dangerous voltages and currents due to resonance may materialize. In this sense, the circuit in FIG. 3 is also free from a "single point of failure", therefore.

It is also conceivable in this case that the dimensions of the components are selected such that, in the case of a pre-determined bias voltage at the PIN diode DP, a resonance at the Larmor frequency occurs. This has the advantage that with an interruption of the voltage, the resonance circuit is automatically detuned but also necessitates a permanent supply with the voltage during reception.

As in FIG. 2, FIG. 3 also indicates by way of the dotted lines, in addition to the printed conductor, the path of the direct voltage/direct current for actuation of the active detuning facility 51. Neither of the two figures show a radio frequency decoupling by way of, for example, inductors at the detuning connection 54 either, which prevent the magnetic resonance signal from being short-circuited or attenuated via this connection.

In FIG. 3, by way of example, the capacitor in FIG. 2, which is connected in series to the diodes $D_S$, is also designed redundantly. Here, in each case two individual capacitors are connected in parallel in pairs and these pairs are in turn connected in series. In this way, both the short-circuiting of a capacitor and also in the event of a contact problem, and therewith capacitance tending toward zero of an individual capacitor, both a sufficient total capacitance of the system including four capacitors and a sufficient residual capacitance are available for detuning.

This redundancy concept may be applied to different components necessary for detuning and also to diodes and inductors. Depending on the failure performance, for example, in the case of a diode against short-circuit, a second diode may be connected in series or in the case of an inductor against a disconnection, for example, due to mechanical load, a parallel inductor may be provided, which is configured to be sufficiently large.

The function of the individual detuning facilities is as already described in relation to FIG. 2.

Figure 4:
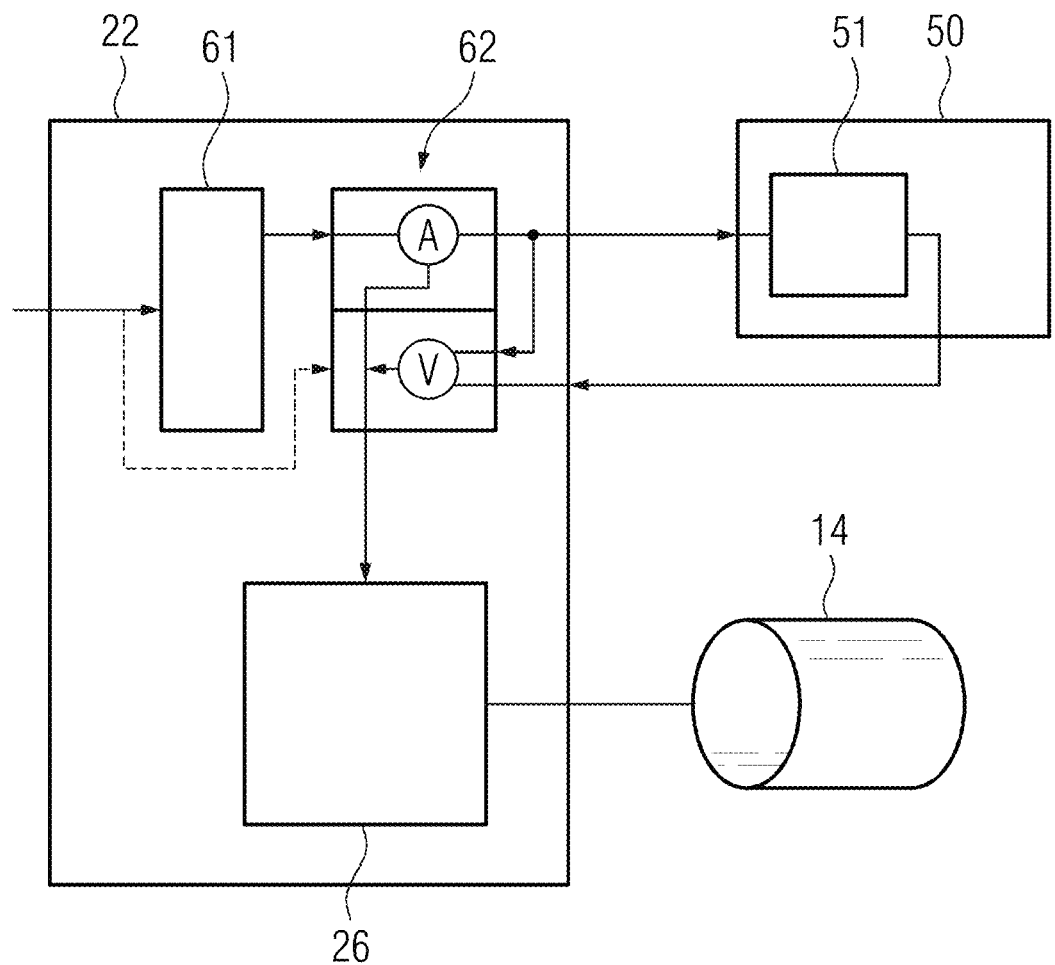
FIG. 4 depicts one possible embodiment of a local coil actuation and local coil monitoring of a magnetic resonance tomography scanner.

FIG. 4 depicts one possible embodiment of a local coil actuation 61 and a local coil monitoring 62 and their cooperation with a radio frequency unit 22 or its transmitter 26 and the local coil 50.

The active detuning facilities presented in FIGS. 2 and 3 may be actuated in the blocking direction of the PIN diode $D_P$ with a direct voltage, while for a radio frequency short-circuit via the PIN diode $D_P$, the diode is supplied with a forward current. Depending on the operating mode, the local coil actuation 61 may optionally generate a current-limited output signal or a constant current for this or a constant voltage. In order to accelerate the switching processes, it is also conceivable to apply transient currents or voltages after the switchover. The desired status of the local coil 50 is specified via a signal link by the controller 23 as a function of the magnetic resonance sequence of the local coil actuation 61 that has just taken place, and this is indicated by the arrow from the left in the local coil actuation 61.

In the embodiment in FIG. 4, the output signal of the local coil actuation 61 is fed to the local coil monitoring 62. For monitoring the current, a current sensor or current measuring device is looped into the signal link of local coil actuation 61 and local coil 50 in the local coil monitoring. The return conductor, which may also be carried out, (e.g., by way of a ground line), is not shown for the sake of clarity. The voltage of the output signal is monitored by a voltage sensor or a voltage measuring device of the local coil monitoring 62. This may also be connected via a spur, e.g., with a voltage of 0 volt being provided as the fault, so an interruption of the connection to the voltage measuring device is also identified as a fault. It is also conceivable that, depending on the type of active detuning facility 61, only voltage or current are monitored if only one of the two states: (1) short-circuit due to forward current or (2) change in capacitance due to reverse voltage are used.

It is also conceivable that, as illustrated, a further sensor line supplies a signal in relation to the voltage from the local coil 50. This may be a signal in relation to the voltage at the PIN diode $D_P$, but also, for example, a voltage signal, which indicates an amplitude of the radio frequency voltage in the antenna circuit.

The local coil monitoring 62 evaluates the voltage and/or current signals as is explained below and in the event of a fault emits an alarm signal, which immediately interrupts, for example, a radio frequency emission of the transmitter 26. An interruption via the controller is also conceivable. Suitable signal routing and protocols or logics provide(s) that in the event of a fault in the local coil monitoring 62 and/or controller 23, an interruption likewise occurs and there is no risk to the patient 100.

Recognition of a fault depends on the implementation of the active detuning facility 51 and optionally also the passive detuning facility 52. A case will be described below, which envisages both detuning due to reverse voltage and short-circuiting due to forward current. Depending on the design of the circuit, it may also be provided that only one or a few of the described signal(s) and fault(s) are necessary to provide the safety of the patient 100.

Detuning by way of a reverse voltage is characterized in that a very low reverse current flows with a relatively high voltage of several volts, (e.g., above 5V, 10V, 20V, 50 V, or 100V). The local coil monitoring 62 recognizes proper functioning of the active detuning facility 51 in this operating mode by way of a voltage in a correspondingly high region of several volts with the corresponding polarity for blocking the diode and no, or a very low, current. The status may also be generated by an interruption of the line to the local coil 50 or inside to the active detuning facility 51. To recognize this, the voltage in the local coil 50 may be detected by a sensor or an electrical connection and returned to the local coil monitoring 62. It would also be conceivable, (e.g., by way of a predetermined parallel resistance to the PIN diode), to let a small, predetermined test current flow also in the case of reverse polarity and in this way be able to monitor the integrity of the signal link.

The local coil monitoring 62 evaluates current and/or voltage by comparison with predetermined desired values and emits an alarm signal in the event of a fault. The varying capacitance of the PIN diode $D_P$ may be used for tuning in the case of reception. A voltage range for tuning differs from a much higher voltage for detuning, however, so the local coil monitoring may differentiate by way of suitable desired ranges or a threshold value. Detuning due to forward current differs solely by way of the polarity.

A fault due to short-circuiting, for example, on breakdown of the PIN diode $D_P$, may then be recognized by an excessively high current greater than a desired value or else with a current limitation or high internal resistance of the voltage source, by an inadequate voltage of the output signal of the local coil actuation 61 below a desired value 51.

A further conceivable fault is an interruption of the line between local coil monitoring 62 and active detuning facility 51. This is characterized by a high voltage, which substantially corresponds to the predetermined reverse voltage. Because the current is inherently low in the event of blocking of the diode $D_P$, a line interruption may only be recognized by a parallel resistance to the diode $D_P$ and a current flowing as a result or absent in the event of an interruption. A line interruption in the feed line to the local coil 50 may also be recognized in the event of blocking with a voltage sensor at the PIN diode or a return line to a voltage measurement at the PIN diode $D_P$.

A PIN diode $D_P$ that has become highly resistive owing to a defect may be detected by a voltage sensor during an emission of an excitation pulse in the local coil 50, with the voltage sensor detecting a radio frequency voltage in the antenna coil 55 and returning it to the local coil monitoring 62. If detuning does not occur owing to the defective diode, the radio frequency voltage in the antenna coil 55 increases above a predetermined safe value and the local coil monitoring 62 may output an alarm signal which causes an interruption in emitting. Alternatively, a highly resistive PIN diode $D_P$ is recognized by an interruption of the current flow in the short-circuit mode with forward current, as explained below. If the short-circuit mode is used for detuning during an excitation pulse, recognition by the local coil monitoring 62 is in this case adequate for providing the safety of the patient 100.

In the short-circuit mode of the active detuning facility 51, in other words, when a voltage is applied in the flow direction to the PIN diode $D_P$, a relatively high current, (e.g., greater than 5 mA, 10 mA, 50 mA, 100 mA, or 500 mA), flows on the basis of the diode characteristic curve with low voltage of approx. one to several volt(s). Because an interruption of the current loop, regardless of at which location in the current loop, leads to an interruption of the current flow, a fault cannot be easily recognized. As a result of the interruption the current tends toward zero, and at the same time the voltage remains constant or even increases if the current is limited by a resistor or a constant current source. Accordingly, the local coil monitoring 62 recognizes the fault due to a voltage threshold value being exceeded and/or a current threshold value not being attained.

A fault in the passive detuning facility 52 may be detected by the local coil monitoring 62, on the other hand, by way of a sensor for the radio frequency voltage in the antenna coil 55. If the active detuning facility 51 is not actuated and at the same time an excitation pulse, for example from the transmitter 26 via body coil 14, leads to an increase in the radio frequency voltage above a predetermined threshold value, for example greater than 1 $V_{PP}$, $2V_{PP}$, $5V_{PP}$ or $10V_{PP}$, it may be assumed that there is a fault in the passive detuning facility 52 and the local coil monitoring 62 emits an alarm signal. This also applies in the case of a double fault, if, for example, the active detuning facility 51 is actuated owing to a defect but does not lead to detuning of the resonance circuit of the antenna coil 55.

When evaluating the measuring signals, the local coil monitoring 62 may also take into account the set operating mode of the active detuning facility 51, which is specified by the controller 23 as a function of the development of a magnetic resonance sequence of the local coil actuation 61 by way of a signal, as is indicated by the arrow from the left in the local coil actuation 61.

The local coil 50 may be detuned during emission of an excitation pulse by the transmitter 26. This may occur by way of a forward current through the PIN diode $D_P$, so the components are connected in series with the diode $D_P$ in relation to the radio frequency in the resonance circuit, for example, parallel to $C_{R2}$ in FIG. 2 and parallel to $C_{R3}$ in FIG. 3. If an interruption of the current is recognized in this operating mode, the local coil monitoring 62 emits the alarm signal for the interruption of the emission to the transmitter 26.

Detuning due to a high voltage in the blocking direction owing to changed capacitance of the PIN diode $D_P$ is also conceivable. If the local coil actuation 61 is placed in this state by the controller 23 and a fault recognized by the local coil monitoring 62, (e.g., due to a missing, insufficiently high reverse voltage), then, here too, the local coil monitoring 62 interrupts emission through the emitter 26.

Particular test states, (e.g., to test the passive detuning facility 52 by way of a test pulse), are also conceivable. In this case, active detuning is conventionally not activated during the test pulse and no forward current flows or no high reverse voltage is applied. As the local coil monitoring 62 identifies the operating mode of the local coil actuation 61 via a signal input, in this case, an alarm signal may be suppressed by the local coil monitoring to enable the test and still provide the safety of the patient 100 during operation.

Conversely, a simple local coil monitoring 62 without signal link to the local coil actuation 61, (e.g., without knowledge of the operating state), is also sufficient for safe operation. This may be achieved in that a sensor directly detects the radio frequency voltage at the antenna coil 55 and, when a threshold value is exceeded, the local coil monitoring 62 interrupts emission through the transmitter 26. Detuning due to a forward current may also be effectively monitored owing to the closed current loop.

In FIG. 4, the local coil monitoring 62 is arranged in the radio frequency unit 22. A separate unit or an arrangement in the local coil 50 may also be conceivable. Fail-safe transmission of the alarm signal to the transmitter 26 would then have to be guaranteed, however. This may be achieved by a signal line, which without connected local coil 50 blocks the transmitter 26, (e.g., by way of a pull-up resistor in the transmitter), which in the good case is actively pulled to ground by the local coil monitoring 62 and in the event of a fault becomes highly resistive. The high level at the signal input of the transmitter then interrupts emission. Digital protocols, in which transmission is provided and/or in the absence of regular messages emitting is likewise interrupted, are also conceivable, however.

For the body coil 14, for example, detuning during the transmit phase or on receipt of the magnetic resonance signal via the body coil or detuning during receipt of the magnetic resonance signal via the local coil 50 by way of a body coil control is similarly conceivable. The circuit may be similar to that of the local coil actuation 61 illustrated in FIG. 3. A body coil 14 as a transmit coil may be detuned during an excitation pulse in order to irradiate the excitation pulse as efficiently as possible, and when receiving, detunes in order to not attenuate the magnetic resonance signal when local coils 50 receive it and to reduce noise irradiation, for example, of the end stages. In this sense, transmission and reception are interchanged here in the case of the body coil 14 with respect to the local coil actuation 61 for local coil 50.

In a manner similar to that shown in FIG. 4, a body coil monitoring system may then monitor the function of tuning or detuning elements of the body coil 14, for example, by way of permissible or faulty combinations of applied voltages and flowing currents, as already described for the local coils, and in the case of malfunctioning, interrupt a radio frequency emission or sequence.

FIG. 5 depicts one possible embodiment of a method.

In act S10, the controller 23 actuates an active detuning facility 51 of the local coil 50 via the local coil actuation 61. This conventionally occurs in the course of an image recording sequence in order to protect the local coil 50 and the patient 100 against danger due to induced voltages and/or currents in the antenna coil 55. Depending on the embodiment of the local coil 50 and the active detuning facility 51, this may occur by way of a reverse voltage of several 10s to over 100 volts at the PIN diode $D_P$ or also by way of a forward current through the PIN diode $D_P$ to make this conductive for a radio frequency signal. It is also conceivable for a test to occur without actuation, for example, if the radio frequency voltage at the antenna coil is detected by a sensor and the effect of the passive detuning facility 52 is to be tested.

In act S20, the controller 23 actuates the transmitter 26 of the radio frequency unit 22. This conventionally occurs in the course of an image recording sequence to excite the nuclear spins in the patient 100. This act may occur in the course of monitoring during operation to then protect the patient 100 from harm during the excitation pulse. It is also conceivable that in the framework of the method, permanent monitoring occurs without excitation pulse. For example, the resonance circuit of the antenna coil 55 may be tuned in frequency by a reverse voltage. If this voltage is reduced or short-circuited by a low load resistance of the local coil 50, a defective PIN diode $D_P$ with internal short-circuit will be suspected. A periodic or permanent test of the active detuning facility 51 by way of a current or a voltage in the forwards direction of the PIN diode $D_P$ is also conceivable. If the current is too low, there may be an interruption of the current circuit.

In act S30, the local coil monitoring 62 receives a fault signal at a detuning monitoring input, which signals malfunctioning of the active detuning facility 51 and/or the passive detuning facility 52 of the local coil 50. The detuning monitoring input may be the inputs for voltage measurement and/or current measurement in signal link with the detuning connection 54 of the active detuning facility 51. Separate current or voltage sensors, which monitor currents or voltages in the local coil are also conceivable. By way of example, a voltage sensor for a radio frequency voltage in the antenna coil 55 has already been explained. A signal link, via which one or more measured value(s) is/are transmitted from the local coil 50 in an analog or a digital manner to the local coil monitoring 62 is also conceivable with current or voltage monitoring in the local coil.

The local coil monitoring 62 determines, by way of a comparison of the fault signal with one or more predetermined desired value(s), if the fault signal signals malfunctioning. This evaluation may occur as a function of an operating mode of the local coil actuation 61, the controller 23, and/or the progress of an image recording sequence. Different fault conditions have already been explained in detail in relation to FIG. 4 and for this reason reference shall merely be made to them at this point.

Finally, in act S40, the local coil monitoring 62 interrupts a radio frequency emission through the transmitter 26. An interruption is here also taken to mean prevention of a future radio frequency transmission. This may occur in that the local coils 50 prevents a supply of energy or an actuation signal to the transmitter 26 by way of a switch or a relay. A signal via a signal path secured against failure and/or a protocol, by which emission without active approval by the local coil monitoring is prevented, is also conceivable, however.

In one embodiment, the method may similarly recognize malfunctioning of body coil tuning or detuning and interrupt a radio frequency emission or prevent or terminate image recording sequence using the body coil control and body coil monitoring system.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

Although the disclosure has been illustrated and described in detail with reference to the exemplary embodiments, it is not limited by the disclosed examples and a person skilled in the art may derive other variations herefrom without departing from the scope the disclosure.

The invention claimed is:

1. A local coil comprising:
   an active detuning facility; and
   a passive detuning facility,
   wherein the passive detuning facility and the active detuning facility have substantially separate circuits,
   wherein a component necessary for detuning is configured redundantly in the active detuning facility, and
   wherein an additional component necessary for detuning is configured redundantly in the passive detuning facility.

2. The local coil of claim 1, further comprising:
   at least one monitoring signal output for at least one monitoring signal,
   wherein the local coil is configured to signal with the at least one monitoring signal a functional status of the passive detuning facility or the active detuning facility.

3. The local coil of claim 1, further comprising:
   at least one monitoring signal output for at least one monitoring signal,
   wherein the local coil is configured to signal with the at least one monitoring signal a functional status of the passive detuning facility and the active detuning facility.

4. A magnetic resonance tomography scanner for a local coil having an active detuning facility and a passive detuning facility, wherein the magnetic resonance tomography scanner comprises:
   a local coil actuation; and
   a local coil monitoring,
   wherein the local coil actuation and the local coil monitoring have substantially separate circuits.

5. The magnetic resonance tomography scanner of claim 4, further comprising:
   a controller,
   wherein the local coil monitoring has a first direct signal link to the controller, and
   wherein the controller is configured to interrupt a radio frequency emission in response to a warning signal of the local coil monitoring via the first direct signal link.

6. The magnetic resonance tomography scanner of claim 5, wherein the controller has a second direct signal link to a radio frequency controller, and
   wherein the radio frequency controller is configured to directly interrupt the radio frequency emission in response to an interrupt signal of the controller via the second direct signal link.

7. A system comprising:
   a local coil having an active detuning facility, a passive detuning facility, and at least one monitoring signal output for at least one monitoring signal, wherein the passive detuning facility and the active detuning facility have substantially separate circuits, and wherein the local coil is configured to signal with the at least one monitoring signal a functional status of the passive detuning facility and/or the active detuning facility; and
   a magnetic resonance tomography scanner having a local coil actuation and a local coil monitoring, wherein the local coil actuation and the local coil monitoring have substantially separate circuits, wherein the local coil monitoring has a detuning monitoring input that has a direct signal link to the at the least one monitoring signal output of the local coil.

8. The system of claim 7, wherein the magnetic resonance tomography scanner further comprises a controller,
   wherein the local coil monitoring has a first direct signal link to the controller, and wherein the controller is configured to interrupt a radio frequency emission in response to a warning signal of the local coil monitoring via the first direct signal link, and wherein the local coil monitoring is configured to emit the warning signal to interrupt the radio frequency emission to the controller via the first direct signal link in case of a fault signal at the detuning monitoring input, which signals malfunctioning of the active detuning facility and/or the passive detuning facility of the local coil.

9. A method for operating a system comprising a magnetic resonance tomography scanner and a local coil, wherein the magnetic resonance tomography scanner has a local coil actuation and a local coil monitoring, wherein the local coil actuation and the local coil monitoring have substantially separate circuits, wherein the local coil has an active detuning facility, a passive detuning facility, and at least one monitoring signal output for a monitoring signal, wherein the passive detuning facility and the active detuning facility have substantially separate circuits, the method comprising:

receiving a fault signal at a detuning monitoring input of the local coil monitoring, which signals malfunctioning of the active detuning facility and/or the passive detuning facility of the local coil; and interrupting a radio frequency emission by the local coil monitoring.

10. The method of claim 9, further comprising:
emitting, by the magnetic resonance tomography scanner, a radio frequency transmission prior to the receiving of the fault signal.

11. The method of claim 10, further comprising:
actuating, by the magnetic resonance tomography scanner, the active detuning facility in the local coil prior to the receiving of the fault signal.

12. The method of claim 9, further comprising:
actuating, by the magnetic resonance tomography scanner, the active detuning facility in the local coil prior to the receiving of the fault signal.

13. A magnetic resonance tomography scanner comprising:
a body coil control; and
a body coil monitoring system,
wherein the body coil control and the body coil monitoring system have substantially separate circuits.

\* \* \* \* \*